United States Patent
Bobotas et al.

(10) Patent No.: US 6,930,119 B2
(45) Date of Patent: Aug. 16, 2005

(54) LIQUID PHARMACEUTICAL COMPOSITION

(75) Inventors: George Bobotas, Tarpon Springs, FL (US); Abdel A. Fawzy, Dracut, MA (US)

(73) Assignee: Reliant Pharmaceuticals, Inc., Liberty Corner, NJ (US)

( * ) Notice: Subject to any disclaimer, the term of this patent is extended or adjusted under 35 U.S.C. 154(b) by 324 days.

(21) Appl. No.: 10/198,271

(22) Filed: Jul. 17, 2002

(65) Prior Publication Data

US 2004/0013693 A1 Jan. 22, 2004

(51) Int. Cl.$^7$ ............... A61K 31/425; A61K 47/00
(52) U.S. Cl. ............... 514/365; 424/439; 514/779; 514/974
(58) Field of Search ............... 424/686, 687, 424/600, 690, 451, 464, 489, 439, 456, 689; 514/819, 365, 779, 974, 400

(56) References Cited

U.S. PATENT DOCUMENTS

| | | | | |
|---|---|---|---|---|
| 3,492,131 A | * | 1/1970 | Schlatter | 426/548 |
| 4,996,222 A | * | 2/1991 | Carlin et al. | 514/400 |
| 5,007,790 A | | 4/1991 | Shell | |
| 5,456,918 A | * | 10/1995 | Quirk et al. | 424/451 |
| 5,811,123 A | | 9/1998 | Fuisz | |
| 5,976,578 A | * | 11/1999 | Beyerle et al. | 424/686 |

FOREIGN PATENT DOCUMENTS

| | | |
|---|---|---|
| DE | 39 31 215 A | 3/1990 |
| WO | WO 95 01780 A | 1/1995 |
| WO | WO 95 01795 A | 1/1995 |

OTHER PUBLICATIONS

Washington N et al., "Effect of Alginate and Alginate–Cimetidine Combination Therapy on Stimulated Postprandial Gastro–Oesophageal Reflux." Journal of Pharmacy and Pharmacology, London, GB, vol. 47, no. 11, pp. 879–882 (1995).

* cited by examiner

*Primary Examiner*—Thurman K. Page
*Assistant Examiner*—Micah-Paul Young
(74) *Attorney, Agent, or Firm*—Gibbons, Del Deo, Dolan Griffinger and Vecchione

(57) ABSTRACT

This invention relates to new pharmaceutical compositions and methods for their preparation, and in particular it relates to taste-masked liquid compositions comprising a solution of a histamine $H_2$-antagonist complexed with an alginate and also containing a humectant. The solution is buffered to a pH of between about 6 to 7. The inventive solution may be flavored and sweetened and preserved.

16 Claims, No Drawings

LIQUID PHARMACEUTICAL COMPOSITION

BACKGROUND OF THE INVENTION

1. Field of the Invention

This invention relates to new pharmaceutical compositions and methods for their preparation, and in particular it relates to taste-masked liquid compositions comprising a solution of a histamine $H_2$-antagonist complexed with an alginate.

2. Description of Related Art

The histamine $H_2$-receptor antagonists are a highly successful class of drugs. These compounds are widely prescribed to treat gastrointestinal disorders and are usually administered orally. Unfortunately, most members of this class have the drawback of having an extremely disagreeable taste. The art has recognized this problem and has applied many different approaches to trying to solve this problem.

U.S. Pat. No. 4,996,222 describes a pharmaceutical suspension of cimetidine having a pH of at least 7 wherein substantially all of the cimetidine is in the polymorph B crystalline form. The composition will contain a suspending agent. The composition may contain alginate as a thickening agent. Examples of suspending agents include xanthan gum, hydroxypropylmethylcellulose, methylcellulose, carageenan, sodium carboxymethyl cellulose, and sodium carboxymethyl cellulose/microcrystalline cellulose mixtures, particularly sodium carboxymethyl cellulose/microcrystalline cellulose mixtures.

Thus, in U.S. Pat. No. 5,576,344, a process for reducing the adverse taste and malodor associated with $H_2$-receptor antagonist nizatidine is described. The process involves forming an aqueous solution of the compound and subjecting the solution to elevated temperatures sufficient for a period sufficient to cause a reduction in the adverse taste and/or malodor.

U.S. Pat. No. 5,622,980 describes a solid composition for oral administration of an $H_2$-receptor antagonist which composition includes a silicate taste-masking agent capable of forming an adsorbate complex with the $H_2$-antagonist wherein the complex exhibits a non-bitter taste. The complex inhibits the release of the $H_2$-antagonist in the oral cavity.

Chewable tablets containing unpleasant tasting medicaments such as cimetidine are disclosed in U.S. Pat. No. 5,275,823. The palatability of the tablets is improved by including certain hygroscopic water-insoluble substances as extragranular excipients. Such excipients include cellulose derivatives, sodium starch glycolate and cross-linked polyvinylpyrrolidine.

A chewable dosage form containing a histamine $H_2$-receptor antagonist in an amount which is effective to treat a gastrointestinal disorder is provided in a palatably acceptable form in U.S. Pat. No. 6,270,807. The dosage form comprises granules containing the histamine H2-receptor antagonist, which are provided with a taste-masking coating comprising a water-insoluble, water-permeable methacrylate ester copolymer in which the coating is applied to the granules in an amount which provides a taste-masking effect for a relatively short period during which the composition is being chewed by a patient, but which allows substantially immediate release of the histamine $H_2$-receptor antagonist after the composition has been chewed and ingested.

U.S. Pat. No. 6,197,348 discloses a taste-masked pharmaceutical composition. There is provided a taste masked oral pharmaceutical composition including: a pharmaceutically active ingredient having a pH-dependent solubility; a polymer encapsulating said pharmaceutically active ingredient, said polymer having a quaternary ammonium functionality; a suspending medium for suspending the encapsulated pharmaceutically active ingredient, said medium adjusted to a predetermined pH at which the pharmaceutically active ingredient remains substantially insoluble; and wherein the pharmaceutically active ingredient is taste masked by the combination of the polymer and suspending medium.

Taste masked immediate release micromatrix powders are described in U.S. Pat. No. 6,153,220. Taste masked immediate release micromatrix powders can be formed by spray drying the drug and cationic copolymer whereas sustained release micromatrix powders can be formed by granulating controlled release powders, which can be made by spray drying the drug with a retarding polymer, with the cationic copolymer. These powders containing drugs with poor organoleptic properties can be incorporated into conventional oral dosage forms such as sprinkles, suspension, fast melt tablets, chewable tablets or effervescent tablets.

BRIEF SUMMARY OF THE INVENTION

This invention relates to new pharmaceutical compositions and methods for their preparation, and in particular it relates to taste-masked liquid compositions comprising a solution of a histamine $H_2$-antagonist complexed with an alginate and also containing a humectant. The solution is buffered to a pH of between about 6 to 7. The inventive solution may be flavored and sweetened and preserved.

DETAILED DESCRIPTION OF THE INVENTION

Histamine $H_2$-antagonists have been used for a number of years in the treatment of duodenal and benign gastric ulceration, recurrent and stomal ulceration, esophageal reflux disease and other conditions where reduction of gastric acid has been shown to be beneficial, for example persistent dyspeptic symptoms with or without ulceration. The members of this class of medicines have a very bitter taste and palatability of oral compositions is a major consideration and has been a major problem in the preparation of liquid oral compositions. Although the inclusion of a bitter tasting medicine in a coated tablet or within a capsule overcomes the problem of offensive taste, many adults and many children that have difficulty swallowing tablets or capsules cannot benefit from these dosage forms.

Solutions of histamine $H_2$-antagonists have been found to be unpalatable. We have found that by preparing a solution of $H_2$-antagonists with an alginate, a taste-masked composition is formed. The taste-masking is believed to result a complex being formed between the $H_2$-antagonist and the alginate. The taste masking effect is augmented by the addition of sweetener, flavor, artificial sweetener enhancer and a humectant.

It is clear that there has been a need for compositions of histamine $H_2$ antagonists which are liquid based and are palatable. Histamine $H_2$-antagonists are believed to be absorbed almost exclusively in the small intestine and liquid-based compositions offer the possibility that they could be absorbed more quickly and more efficiently than tablet compositions, particularly tablet compositions which have been coated to minimize unpleasant tastes.

The composition of the present invention can be prepared by mixing an alginate dispersion in a humectant and preservative solution with a buffered solution of histamine $H_2$ antagonist then adding the sweetener, artificial sweetener enhancer (optional) and flavor then adjusting the pH to about 6.5±0.5 and adding sufficient purified water to bring the solution to its final volume.

Examples of Sweeteners Include:

A. Water-soluble sweetening agents such as monosaccharides, disaccharides and polysaccharides such as xylose, ribose, glucose, mannose, galactose, fructose, dextrose, sucrose, sugar, maltose, partially hydrolyzed starch, or corn syrup solids and sugar alcohols such as sorbitol, xylitol, mannitol and mixtures thereof.

B. Water-soluble artificial sweeteners such as the soluble saccharin salts, i.e., sodium, or calcium saccharin salts, cyclamate salts, acesulfam-K, ammonium glycyrrhizinate, dipotassium glycyrrhizinate and the like, and the free acid form of saccharin.

C. Dipeptide based sweeteners such as L-aspartylphenylalanine methyl ester and materials described in U.S. Pat. No. 3,492,131 and the like.

A water soluble sweetener (A.) will usually be present in an amount corresponding to about 20 to 50% w/v of the total composition, the amount depending in part upon whether other sweetener ingredients are present and the level of sweetness desired.

When sugar is used as the sweetener, typically it is present from about 20% to about 50% w/v of the composition. It will be appreciated that combinations of sweeteners can be used.

The sweetening agents when used, may also be used alone or in combination with each other.

Humectants such as glycerol and propylene glycol are present in the composition. Typically the total quantity of humectant present is in the range of about 8 to 15% w/v. Thus, for example, propylene glycol and glycerol can each be present individually or in combination.

An artificial sweetness enhancer may optionally be utilized in the present invention. When an artificial sweetness enhancer is utilized, it may be present in an amount from about 0.05% to about 1.5% w/v of the final composition. Preferably, the artificial sweetness enhancer will be present in an amount from about 0.1% to about 1% w/v of the final composition. Typical artificial sweetness enhancer would be Pro Sweet® manufactured by the Virginia Dare company and Sweet AM® from Flavors of North America.

It is preferred that the liquid compositions of the present invention contain preservatives to prevent microbial contamination. Examples of preservatives are the alkylparabens, particularly methylparaben, propylparaben and butylparaben. The amount of preservative generally utilized will vary depending upon the preservative selected and may for example range from about 0.05% to about 1.5% w/v of the final composition. Preferably, the preservative will be present in an amount from about 0.01% to about 0.1% w/v of the final composition.

Suitable flavorings include both natural and artificial flavors, and mints such as peppermint, menthol, artificial vanilla, cinnamon, various fruit flavors, both individual and mixed, and the like are contemplated. The flavorings are generally utilized in amounts that will vary depending upon the individual flavor, and may, for example, range in amounts of about 0.01% to about 1% by weight/volume of the final composition. Preferably, the flavorants will be present in an amount of about 0.01% to about 0.1% w/v of the final composition. The flavorants include synthetic flavorants or natural flavorants, such as lemon, lime, orange, menthol, strawberry, bubblegum, and the like.

The optional colorants useful in the present invention, include the pigments such as titanium dioxide, that may be incorporated in amounts of up to about 1% by weight/volume, and preferably up to about 0.6% by weight/volume. Also, the colorants may include other dies suitable for food, drug and cosmetic applications, and known as F.D. & C. dyes and the like. The materials acceptable for the foregoing spectrum of use are preferably water-soluble. Illustrative examples include indigoid die, known as F.D. & C. Blue No. 2, which is the disodium salt of 5,5'-indigotindisulfonic acid. Similarly, the dye known as F.D. & C. Green No. 1, comprises a triphenylmethane dye and is the monosodium salt of 4-[4-Nethyl-p-sulfobenzylamino) diphenylmethylene]-[1-(N-ethyl-N-p-sulfoniumbenzyl)-2, 5-cyclohexadienimine]. A full recitation of all F.D. & C. and D. & C. and their corresponding chemical structures may be found in the Kirk Othmer Encyclopedia of Chemical Technology, in Volume 5, at Pages 857–884, which text is accordingly incorporated herein by reference.

The liquid compositions of the present invention may optionally contain ingredients which improve its taste, such as sodium chloride and natural and artificial flavour enhancers such as monosodium glutamate, soy sauce and the like.

The liquid compositions of the present invention contain from about 0.5 to 5% w/v histamine $H_2$-antagonist. The histamine $H_2$ antagonist is selected from the group consisting of nizatidine, famotidine, ranitidine, and cimetidine.

The ratio of histamine $H_2$-antagonist to alginate is about 1:0.1 to about 1:0.6 w/w and preferably about 1:02 to about 1:04 w/w.

Alginates are a hydrophilic, colloidal polysaccharide in the form of salts such as sodium, calcium, magnesium and other bases. The preferred form of alginate is an alkali metal salt most preferably the sodium salt. Alginate is present in an amount of about 20% to about 40% w/w of the histamine $H_2$-antagonist.

Buffers: The buffer comprises acids and their base salts for example, citric acid (e.g., citric acid anhydrous), tartaric acid, malic acid, phosphoric acid and the like and their respective salts.

Obviously, numerous modifications and variations of the present invention are possible in light of the above teachings and the invention is not limited to the example herein. It is therefore understood that within the scope of the appended claims, the invention may be practiced otherwise than as specifically described herein.

In one preferred embodiment of the invention there is provided a composition containing 0.5 to 2.5% w/v of histamine $H_2$-antagonist. In another preferred embodiment, the histamine $H_2$-antagonist is nizatidine.

EXAMPLE

A Sample Nizatidine Formulation:

| Component | per 100 ml. % w/v |
| --- | --- |
| Nizatidine | 0.5 to 2.5 |
| Humectant | 8 to 15 |
| Sodium alginate | 0.1 to 1.5 |
| Sodium chloride | 0.1 to 0.5 |
| Artificial sweetener | 0.1 to 0.5 |

-continued

| Component | per 100 ml. % w/v |
|---|---|
| Buffer | 0.5 to 1.5 |
| Preservative | 0.05 to 0.5 |
| Natural sweetener | 20 to 50 |
| Flavor | 0.01 to 1.0 |
| Artificial sweetness enhancer | 0.1 to 0.9 |
| Water to 100% v/v | QS |

Process

Premix 1:

Add with mixing the preservative(s) to the humectant which is contained in a suitable vessel and has been preheated to about 60° C.±5° C. and continue mixing until dissolved. Cool the solution to about 50° C.±5° C. then slowly add the alginate with continued mixing to uniformly disperse the alginate in the liquid.

In a second vessel, add an amount of purified water equal to about 64% of the final batch volume. Add the following ingredients in the order listed below, with continuous mixing and not adding the next ingredient until the current added ingredient is completely dissolved.

1. Flavor enhancer (salt)
2. Artificial sweetener
3. Buffering agent (basic portion first if a two component buffer)
4. Buffering agent (acidic portion if applicable)
5. Histamine H sub 2 antagonist
6. Premix 1
7. Sweetener
8. Artificial sweetener enhancer
9. Flavor
10. EDTA (optional)

Stop mixing and pre qs to 95% of the final batch volume then mix until the solution is uniform. Measure the pH (use temperature compensation to RT) and adjust the pH if necessary to 6.5. If the pH is greater than 6.5, adjust by adding citric acid solution 20% and mix well. If the pH is less than 6.5, adjust by adding sodium hydroxide 1N and mix well. Discontinue mixing and qs to the final batch volume with purified water.

We claim:

1. A pharmaceutical composition for the oral administration of a therapeutically effective amount of nizatidine in the form of the free base, wherein said composition exhibits a non-bitter taste, said composition comprising a solution of:
   a therapeutically effective amount of nizatidine, and
   an alginate taste-masking agent capable of forming a complex there with,
wherein the ratio of nizatidine to the alginate is from 1:0.1 to 1:0.6 weight to weight, and further wherein the pH of the solution is from pH6.0 to 7.0.

2. The pharmaceutical composition according to claim 1, wherein said alginate taste-masking agent comprises sodium alginate.

3. The pharmaceutical composition according to claim 1, wherein the ratio of nizatidine to alginate is about 1:0.2 to about 1:0.4 weight:weight.

4. The pharmaceutical composition according to claim 1, further comprising a flavoring agent selected from the group consisting of natural and artificial flavors and mints.

5. The pharmaceutical composition according to claim 1 further comprising a sweetening agent selected from the group consisting of water-soluble natural sweetening agents, water-soluble artificial sweetening agents and mixtures thereof.

6. The pharmaceutical composition according to claim 5, wherein said water-soluble natural sweetening agent is selected from the group consisting of xylose, ribose, glucose, mannose, galactose, fructose, dextrose, sucrose, sugar, maltose, partially hydrolyzed starch, corn syrup solids, sorbitol, xylitol, mannitol and mixtures thereof.

7. The pharmaceutical composition according to claim 5, wherein said artificial sweetening agent is L-aspartylphenylalanine methyl ester.

8. The pharmaceutical composition according to claim 5, wherein said water-soluble artificial sweetening agent is selected from the group consisting of: sodium, or calcium saccharin salts, cyclamate salts, acesulfam-K, ammonium glycyrrhizinate, dipotassium glycyrrhizinate-and the free acid form of saccharin.

9. The pharmaceutical composition according to claim 4, wherein said flavoring agent is present in from about 0.01% to about 1% by weight/volume of the final composition.

10. The pharmaceutical composition according to claim 4, wherein said flavoring agent is one or more members selected from the group consisting of: peppermint, menthol, artificial vanilla, cinnamon, lemon, lime, orange, menthol, strawberry and bubblegum.

11. The pharmaceutical composition according to claim 1, further comprising a humectant.

12. The pharmaceutical composition according to claim 11, wherein the humectant is present in an amount from 8 to 15 percent w/v of the final composition.

13. The pharmaceutical composition according to claim 11, wherein the humectant is selected from the group consisting of glycerol, propylene glycol and mixtures thereof.

14. The pharmaceutical composition according to claim 1, wherein the pH of the solution is from pH 6.25 to 6.75.

15. The pharmaceutical composition according to claim 1, further comprising an artificial sweetness enhancer in from about 0.05 to about 1.5 percent w/v of the final composition.

16. The pharmaceutical composition according to claim 1, further comprising EDTA in an amount from about 0.05% w/v to about 0.1% w/v.

* * * * *